United States Patent
Martinis et al.

(10) Patent No.: US 10,566,079 B2
(45) Date of Patent: Feb. 18, 2020

(54) CHARACTERIZATION OF COMPLEX HYDROCARBON MIXTURES

(71) Applicants: Jorge M. Martinis, Bryan, TX (US); Charles C. Solvason, Bryan, TX (US)

(72) Inventors: Jorge M. Martinis, Bryan, TX (US); Charles C. Solvason, Bryan, TX (US)

(*) Notice: Subject to any disclaimer, the term of this patent is extended or adjusted under 35 U.S.C. 154(b) by 0 days.

(21) Appl. No.: 15/904,334

(22) Filed: Feb. 24, 2018

(65) Prior Publication Data
US 2019/0267116 A1    Aug. 29, 2019

Related U.S. Application Data

(63) Continuation of application No. 14/287,980, filed on May 27, 2014, now abandoned.

(60) Provisional application No. 61/886,756, filed on Oct. 4, 2013.

(51) Int. Cl.
| | |
|---|---|
| *G06G 7/48* | (2006.01) |
| *G16C 20/30* | (2019.01) |
| *G16C 20/40* | (2019.01) |

(52) U.S. Cl.
CPC ............ *G16C 20/30* (2019.02); *G16C 20/40* (2019.02)

(58) Field of Classification Search
None
See application file for complete search history.

(56) References Cited

U.S. PATENT DOCUMENTS

| | | | | |
|---|---|---|---|---|
| 9,063,115 | B2* | 6/2015 | DiSanzo | C10G 35/24 |
| 9,625,439 | B2* | 4/2017 | Saeger | G01N 33/2835 |
| 2009/0105966 | A1* | 4/2009 | Brown | G01N 33/2823 |
| | | | | 702/30 |
| 2012/0290280 | A1* | 11/2012 | Naik | G16C 20/10 |
| | | | | 703/12 |

OTHER PUBLICATIONS

Wipke, W. T., et al. "SECS-simulation and evaluation of chemical synthesis: strategy and planning." ACS Symp. Ser. vol. 61. 1977.*
Ferro, V. R., et al. "Integration of COSMO-based methodologies into commercial process simulators: Separation and purification of reuterin." AIChE Journal 58.11 (2012): 3404-3415.*
Hudebine, D., and Jan J. Verstraete. "Reconstruction of petroleum feedstocks by entropy maximization. Application to FCC gasolines." Oil & Gas Science and Technology—Revue d'IFP Energies nouvelles 66.3 (2011): 437-460.*

* cited by examiner

*Primary Examiner* — Rehana Perveen
*Assistant Examiner* — Nithya J. Moll
(74) *Attorney, Agent, or Firm* — Douglas Baldwin

(57) ABSTRACT

Disclosed are processes for improving the performance of a computer system operating a software program for calculating operating parameters and results of hydrocarbon processing units by providing a method of estimating and consolidating molecular composition components and properties of hydrocarbon mixtures such as petroleum fractions. The method provides a reduced number of representative compounds that closely match the characteristics of the complete molecular composition of the mixture that may be used to increase efficiency of a computer system, improve the operation of refinery process and that may be disposed on non-transitory machine-readable media.

4 Claims, 1 Drawing Sheet

CHARACTERIZATION OF COMPLEX HYDROCARBON MIXTURES

CROSS REFERENCE TO RELATED APPLICATIONS

This application is a continuation in part of U.S. application Ser. No. 14/287,980 filed May 27, 2014 which application claims benefit of Provisional Application Ser. No. 61/886,756 filed Oct. 4, 2013, the content, Figures and disclosure of which are incorporated herein by reference in their entirety for all purposes.

BACKGROUND

Field of Invention

A process for improving the performance of a computer system operating a software program for calculating operating parameters and results of hydrocarbon processing units by providing a method of estimating and consolidating molecular composition components and properties of hydrocarbon mixtures such as petroleum fractions. More specifically, the method provides a reduced number of representative compounds that closely match the characteristics of the complete molecular composition of the mixture that may be used to increase efficiency of a computer system, improve the operation of refinery process and that may be disposed on non-transitory machine-readable media.

Background

Petroleum fractions are mixtures of a huge number of component molecules. This makes detailed analytical characterization on a molecular level extremely difficult, if not impossible, and so costly and time consuming as to be largely impractical. There is a recognized need to have a more detailed molecular characterization of these hydrocarbon mixtures than is available from conventional analysis. This need is especially acute in fundamental kinetic models are used for process simulation. Such models have been developed for various chemical processes, such as steam cracking, pyrolysis, steam reforming, hydrocracking, catalytic cracking, etc. These fundamental kinetic models are able to simulate the chemical kinetics over a wide range of process conditions and for a wide range of feedstock types, by accounting for the occurring chemical reactions as well as for the physical transport phenomena governing the process. (Steven P. Pyl, Kevin M. Van Geem, Marie-Francoise Reyniers, and Guy B. Marin; *Molecular Reconstruction of Complex Hydrocarbon Mixtures: An Application of Principal Component Analysis*; AIChE Journal; December 2010 Vol. 56, No. 12) and (US Published application 2009/0105966, Apr. 23, 2009).

The need for estimating detailed molecular composition of petroleum fractions is well recognized in the art and there have been numerous attempts to develop adequate solutions. Developments by Neurock et al. (1994)[1] and Trauth et al. (1994)[2] have applied molecular reconstruction techniques to approximate individual components in petroleum fractions via stochastic optimization methods. The application of stochastic methods is, however, limited by the computational intensity imposed by the large sampling frequency needed to achieve statistical significance (Verstraete, 2004)[3]. For specific petroleum fractions such as naphthas and gas-oils, Hudebine and Verstraete (2011)[4] have utilized a hybrid stochastic method that maximizes an entropy function with Lagrangian parameters associated with analytical constraints in order to reduce the computational burden. However, the method is strongly dependent on the initial set of molecules which must be chosen and built in relation to the type of petroleum fraction studied. The present invention provides another, more useable process for generating hydrocarbon mixture compositional information.

[1] Neurock M., Nigam A., Trauth D. M., Klein M T. (1994) *Molecular Representation of Complex Hydrocarbon Feedstocks through Efficient Characterization and Stochastic Algorithms*, Chem. Eng. 0.5c L 49,24.4153-4177.
[2] Trauth D. M., Stark S. M., Petti T. F., Neurock M. Klein M. T. (1994) *Representation of the Molecular Structure of Petroleum Resid through Characterization and Monte Carlo Modeling*, Energ. Fuel. 8. 3. 576-580.
[3] Verstraele L I., Revellin N. Dulot H Hudebine D. (2004) *Molecular reconstruction of vacuum gasoils*, Prep. Am. Chem. Soc. Div. Fuel Chem. 49,1,20-21.
[4] Hudebine D. and Verstraele L I., Dulot H.; *Reconstruction of Petroleum Feedstocks by Entropy Maximization. Application to FCC Gasolines*; Oil & Gas Sciebce abs Technology,-Rev.IFP Energies novelles.; 2011

SUMMARY

The present invention is a novel approach to the molecular reconstruction of complex hydrocarbon mixtures that may be used in improving the operation of a computer system running programs programmed to calculate, inter alia, operating parameters and results of hydrocarbon processing units, to improve the operation of petroleum refining operations and which novel approach may be expressed in machine readable language and disposed on non-transitory machine-readable media.

DESCRIPTION OF FIGURES

The Figures represent embodiments and aspects of the invention and are not intended to be limiting of the scope of the invention.

DETAILED DESCRIPTION

Figure 1:
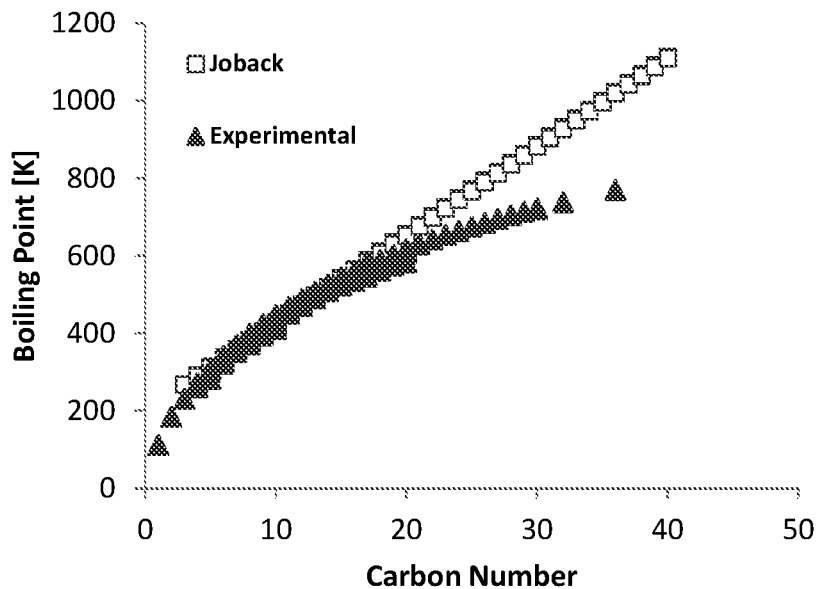
FIG. 1 is a graphical representation the results of a comparison of boiling point results from an embodiment of the invention with analytical results.

The invention, in broad aspect, is expressed in three embodiments: 1) a software system that improves the operation, accuracy and efficiency of a computer system that is programmed to calculate, inter alia, operating parameters and results of hydrocarbon processing units by providing a method of estimating and consolidating molecular composition components and properties of hydrocarbon mixtures such as petroleum fractions; 2) processes for the control of petroleum refinery processes by installing calculated operating parameters to actual operating parameters to change results of operations; and 3) articles of manufacture consisting of a software program disposed on non-transitory machine readable media, which program comprises calculation of molecular composition components and properties of hydrocarbon mixtures such as petroleum fractions. The method provides molecular grouping of complex hydrocarbon mixtures, such as a petroleum fractions (or other chemical hydrocarbon mixture) in a manner that represents the actual molecular composition in a sufficiently simplified manner for convenient utility. The software program(s) described above may include a comprehensive database of identifiable compounds and compound groups and components and from which specific "compound species" (defined below) are selected to develop representation of a chemical mixture composition.

These three embodiments are described in more detail below.

Overview of Important Components and Calculation Methods of the Embodiments

Petroleum mixtures contain thousands, perhaps millions of individual compounds. It is not feasible to analytically obtain a complete list of the molecules. Moreover, even if it were possible the huge number would generally be unmanageable for practical use such as product characterization in programs that calculate, inter alia, operating parameters and results of hydrocarbon processing units by providing a method of estimating and consolidating molecular composition components and properties of hydrocarbon mixtures such as petroleum fractions.

Several techniques exist to generate a reduced set of species to represent petroleum (hydrocarbon) fractions. At present, it is conventional to use pseudo-components based on component boiling points that carry no chemical information, thus making them unsuitable for the simulation of chemical reactors. Other methods use a set of molecules selected by stochastic techniques, where molecules are constructed in terms of moieties and their group contributions and then added to or rejected from the mixture until a good match with the oil fraction properties is achieved. In the latter case, a "group contribution" (addition of properties of individual moieties that may make up a molecule) method is needed to estimate the properties of each species. Consequently, different molecules are only as distinguishable as the group contribution method permits, depending on how detailed their contributions or moieties are.

In general, the available analysis for petroleum fractions will include distillation boiling range curve(s), chromatographic analysis (for chemical families such as paraffins, olefins, naphthenes and aromatics) and sometimes Mass Spectrometry analysis for more detailed analysis.

An aspect of the invention is a process that includes assembling, for a given hydrocarbon mixture, a listing of compounds and "compound species" (as is defined below), together with physical and chemical properties and calculating a molecular fraction composition (or equivalent) that mimics available analytical information (that includes, at least, boiling range analysis) for the mixture.

As used herein and in the claims "compound species" is a collection of molecules in chemical equilibrium which, for all practical purposes, can be treated as a pure species for the calculation of unit operations in a process simulation program that does not involve chemical reactions. In effect, a compound species is a mixture of fixed composition acting as a single component within a larger mixture that contains it. Development of compound species is a key to reducing the number of species for practical use.

"Comprehensive database" means a database (or other suitable data storage and retrieval means) containing a collection of identifiable compounds and compound species (represented by group contribution moieties) together with physical and chemical properties for each identified pure and compound species selected from the database when needed to match a given sample for which the composition and properties are to be calculated (as representative of the actual molecular composition). The database is accessible by computer means and is maintained in a tangible, not transitory form.

In general, the database will contain hydrocarbon species with carbon numbers within a range of interest. The specific pure and compound species selected depends on the intended purpose of the database. For petroleum refining operations, for example, the database will advantageously contain compounds up to about $C_{40}$. This range is adequate for most purposes since petroleum hydrocarbon species above $C_{40}$ are generally asphaltenes for which detailed individual species identification is currently not possible. It is advantageous to structure the database so that when a compound species is selected, the corresponding pure species contained within it will automatically be excluded and conversely when a pure species is selected the compound species that includes it will be excluded. This aids in preventing confusing duplication of compound or compound species in any subsequent calculation of the representative composition of a given sample.

"Display" as the term is used herein in the context of the results of calculations means any suitable means of exhibiting the data, as for example, by printing or exhibiting on a computer screen or monitor. Additionally, it means the results of adapting the data in a manner that it can be displayed in a more complex system such as the systems utilized in chemical process simulation. An example is to have results of calculated data displayed in a word process system such as Microsoft Word™, or a spreadsheet such as Microsoft Excel™ or a more complete system such as Microsoft Visio™. The results can adapted to be integrated into a chemical process simulation and such as ProMax™ (a chemical process simulation system available from Bryan Research and Engineering of Bryan, Tex.) and displayed on a coupled Excel spreadsheet or Microsoft Visio™.

The following discussion of specific applications illustrates the an aspect of the invention and the steps necessary for construction of a more comprehensive database of the second embodiment. Embodiments of the process of the invention were used to characterize a Jet A-1 fuel in terms of pure and compound species. The bulk of a Jet A-1 fuel is a kerosene oil fraction that boils within the range of 180-300° C. A basic analysis of a Jet A-1 sample is presented in Table 1.

This oil fraction is a complex mixture containing thousands of molecules. Currently, there are not analytical techniques capable of resolving all the components and even if it did exist, no property database would have a fraction of the property values required and no chemical process simulator could handle such a large number of species. Therefore, a reduced set of species that properly represent the entire population of molecules in the mixture is desirable.

TABLE 1

| Jet A-1 sample analysis | |
|---|---|
| Analysis | Jet A-1 |
| Specific Gravity | 0.81 |
| Molecular Weight | 170 |
| Hydrogen Content, wt % | 0.138 |
| Aromatics, vol % | 20.0 |
| Olefins, vol % | <0.1 |
| ASTM D86, vol %/° C. | |
| IBP | 174 |
| 10% | 205 |
| 30% | 218 |
| 50% | 232 |
| 70% | 245 |
| 90% | 258 |
| FBP | 300 |

Example 1

For this particular example, an extended version of the Joback's group contribution method was applied. The Joback method predicts eleven important and commonly used pure component thermodynamic properties from molecular structure only. (Joback K. G., Reid R. C., "Estimation of Pure-Component Properties from Group-Contributions", *Chem. Eng. Commun.*, 57, 233-243, 1987), the teachings of which are incorporated n herein by reference.

Table 2 presents the moieties and their group contributions for the boiling point (Tb) utilized by this method for hydrocarbon species. Thus, for instance, the extended Joback's group contribution method allows the estimation the boiling point of n-butane as:

$$Tb(n\text{-butane}) = 2 \times 23.58(CH_3\text{---}) + 2 \times 22.88(\text{---}CH_2\text{---}) = 92.92 \text{ K}$$

A similar procedure carrying additional functionality was applied to estimate other pure species properties such as critical temperature, critical pressure, critical volume, freezing point, Pitzer acentric factor, etc.

TABLE 2

Extended Joback's Group Contributions to Boiling Point

| Moiety | Tb[K] Contribution |
|---|---|
| $CH_3$--- | 23.58 |
| ---$CH_2$--- | 22.88 |
| >CH--- | 21.74 |
| >C< | 18.25 |
| =$C_D H_2$ | 18.18 |
| ---$C_D H$= | 24.96 |
| >$C_D$= | 24.14 |
| =$C_D$= | 26.15 |
| ---$C_A H$= | 26.73 |
| >$C_A$= | 31.01 |
| ($C_A$) > $C_A$= | 31.01 |
| ($C_N$) > $C_A$= | 31.01 |
| ---$C_N H_2$--- | 27.15 |
| >$C_N H$--- | 21.78 |
| >$C_N$< | 21.32 |
| ($C_N$) > $C_N H$--- | 21.32 |

CA: carbon in aromatic ring
CD: double-bond bearing carbon
CN: carbon in cycloalkane ring A direct consequence of utilizing moieties from a group contribution method is that the population of distinguishable molecules in an oil fraction decreases significantly. For example, the following constructions shows how 2,3-dimethyl-pentane and 2,4-dimethyl-pentane become identical when described in terms of Joback's moieties:

$$2,3\text{-dimethyl-pentane} = 2,4\text{-dimethyl-pentane} = 4 \times (CH_3\text{---}) + 3 \times (\text{---}CH_2\text{---})$$

The general approach to construct and select a set of molecules that could represent the oil fraction mixture is by mathematical sampling. Monte-Carlo and other stochastic techniques typically generate molecules tied to a given probability density distribution (Gaussian, Etc.) following a defined set of building rules. On every attempt to construct a molecule, a moiety is tried and then accepted or rejected according to the building rule. Once constructed, every molecule is added to an equimolar mixture, pure and mixture properties are calculated and tested against the measured properties of the oil fraction. This method produces a different selection of molecules for every oil fraction characterized, offering no consistency when a single species base is required to represent several samples of oil fractions within the same boiling range.

A novel approach of aspects of this invention is to take advantage of the fact that the number of indistinguishable molecules that can be represented for a given group contribution method is substantially less than the original population of molecules present in the oil fraction. Therefore, a set of building rules can be constructed so that all the possible indistinguishable molecules could be constructed. Thus, sampling, or selection of an optimum set is no longer required.

As an example, all possible alkanes within the kerosene approximate carbon range $C_8$-$C_{15}$ are constructed. Based on the group contribution method, only (2) two structural characteristics are necessary to fully describe an alkane: carbon number (n) and number of side chains (s). Whereas the group contribution method provides a subset of four (4) moieties to construct any possible alkane: $CH_3$--- ($m_1$), ---$CH_2$--- ($m_2$), >CH--- ($m_3$) and >C< ($m_4$). After applying constraints to satisfy the conservation of bonding valences and atoms, the following relationships result:

$$n = m_1 + m_2 + m_3 + m_4 \quad \quad 1)$$

$$2n + 2 = 3m_1 + 2m_2 + m_3 \quad \quad 2)$$

$$s = m_3 + 2m_4 \quad \quad 3)$$

$$2 + s = m_1 \quad \quad 4)$$

With boundaries:

$$n = 8, 2, \ldots, 15 \quad \quad 1)$$

$$0 \leq s \leq |2(n-2)/3| \quad \quad 2)$$

$$0 \leq m_4 \leq |s/2| \text{ (degree of freedom)} \quad \quad 3)$$

In general, expressions (1)-(4) constitute a linear system of equations in the integer domain with a rank of three (3), leaving only one degree of freedom. The set of solutions for the moieties {m} given the structural characteristics {n, s}, constructs all the possible molecules that satisfy those structural characteristics.

A simple example is the construction of all the possible $C_5$ alkanes: n=5 and s=0, 1, 2 as shown in Table 3. All possible solutions are found by counting over one degree of freedom ($m_4$) from 0 to |s/2|.

TABLE 3

$C_5$ Alkanes Construction

| n | s | $m_1$ | $m_2$ | $m_3$ | $m_4$ | Formula | Name |
|---|---|---|---|---|---|---|---|
|   |   | 2 + s | n − 2 − 2s + $m_4$ | s − 2$m_4$ | $m_4$ = 0 … |s/2| |   |   |
| 5 | 0 | 2 | 3 | 0 | 0 | $CH_3$---$CH_2$---$CH_2$---$CH_2$---$CH_3$ | n-pentane |
| 5 | 1 | 3 | 1 | 1 | 0 | $(CH_3)_2 CH$---$CH_2$---$CH_3$ | 2-methyl-pentane |
| 5 | 2 | 4 | 0 | 0 | 1 | $(CH_3)_4 C$ | neopentane |

A similar approach is also used for other hydrocarbon families such as alkenes, cycloalkanes, aromatics and naphtheno-aromatics. Further generalization requires additional structural characteristics such as number of aromatic rings, number of substituents, etc.

The iterative construction by a computer program of all possible distinguishable molecules within the kerosene carbon range ($C_8$-$C_{15}$) with a maximum number of side chains and ring substituents of four (4); results in the mixture presented in Table 4.

TABLE 4

Constructed molecules in the $C_8$-$C_{15}$ range

| Hydrocarbon Family | Cores | $C_5$ rings | $C_6$ rings | Aromatic rings | Molecules |
|---|---|---|---|---|---|
| Alkanes | — | — | — | — | 123 |
| Alkenes | — | — | — | — | 389 |
| Cycloalkanes | 1 | 0 | 1 | — | 198 |
| Cycloalkanes | 1 | 0 | 2 | — | 40 |
| Cycloalkanes | 1 | 1 | 0 | — | 267 |
| Cycloalkanes | 1 | 1 | 1 | — | 65 |
| Cycloalkanes | 1 | 2 | 0 | — | 99 |
| Cycloalkanes | 2 | 0 | 2 | — | 24 |
| Cycloalkanes | 2 | 1 | 1 | — | 44 |
| Cycloalkanes | 2 | 2 | 0 | — | 69 |
| Aromatics | 1 | — | — | 1 | 112 |
| Aromatics | 1 | — | — | 2 | 25 |
| Aromatics | 2 | — | — | 2 | 11 |
| Naphtheno-Aromatics | 1 | 0 | 1 | 1 | 64 |
| Naphtheno-Aromatics | 1 | 1 | 0 | 1 | 99 |
| Naphtheno-Aromatics | 2 | 0 | 1 | 1 | 31 |
| Naphtheno-Aromatics | 2 | 1 | 0 | 1 | 58 |
| | | | | | 1718 |

Even though the number of molecules needed to characterize a kerosene sample has been reduced to a minimum by constructing only those molecules that the group contribution method of Joback is capable of distinguishing, a set of 1718 molecule is still too large for any practical application in commercial chemical process simulators. For process simulation purposes, the goal is to further reduce the number of species to less than a few hundred in order to match the average number of components that most compositional analyses can report.

A key to achieve a further reduction in the number of species is to introduce the concept of a compound species. A compound species is a collection of molecules in chemical equilibrium which for all practical purposes can be treated as a pure species for the calculation of any unit operation within a simulation that does not convey chemical reactions. In effect, a compound species is a mixture of fixed composition acting as a single component within a larger mixture that contains it.

As an example, suppose the smoke point of a kerosene sample is to be adjusted to the Jet A-1 fuel specification of 25 mm by passing it as a stream through a bed of alumina particles. It is known that in the presence of acid materials, hydrocarbons are transformed according to the rules of the carbenium ion chemistry and that in the particular case of alkenes, fast methyl- and hydride-transfer elementary steps occur leading to chemical equilibrium for all species with the same number of side chains for a given carbon number.

Based on this premise, 116 species are defined in terms of structural characteristics as shown in Table 5. Among the 116 species defined, there are 32 pure species and 84 compound species containing molecules with equal number of carbons, side chains and substituents in chemical equilibrium.

Furthermore, the set of 1718 molecules previously constructed to represent kerosene samples are mapped into 116 species. In the particular case of the kerosene sample shown in Table 1, the negligible content of olefins allowed the removal of alkene species from the mixture. As a result of mapping, 1010 molecules are accounted to characterize the kerosene sample in terms of 116 species.

TABLE 5

Kerosene composition from pure and compound species definitions

| | Structural Characteristics: | | | | | | | | | | | |
|---|---|---|---|---|---|---|---|---|---|---|---|---|
| | Carbon Number | | Side Chains | | Double Bonds | | Cores | | Aromatic Rings | | Aromatic Substituents | |
| Species | Min | Max | Min | Max | Min | Max | Min | Max | Min | Max | Min | Max |
| Octane | 8 | 8 | 0 | 0 | 0 | 0 | 0 | 0 | 0 | 0 | 0 | 0 |
| SBOctanes | 8 | 8 | 1 | 1 | 0 | 0 | 0 | 0 | 0 | 0 | 0 | 0 |
| DBOctanes | 8 | 8 | 2 | 2 | 0 | 0 | 0 | 0 | 0 | 0 | 0 | 0 |
| TBOctanes | 8 | 8 | 3 | 3 | 0 | 0 | 0 | 0 | 0 | 0 | 0 | 0 |
| MBOctanes | 8 | 8 | 4 | 4 | 0 | 0 | 0 | 0 | 0 | 0 | 0 | 0 |
| Nonane | 9 | 9 | 0 | 0 | 0 | 0 | 0 | 0 | 0 | 0 | 0 | 0 |
| SBNonanes | 9 | 9 | 1 | 1 | 0 | 0 | 0 | 0 | 0 | 0 | 0 | 0 |
| DBNonanes | 9 | 9 | 2 | 2 | 0 | 0 | 0 | 0 | 0 | 0 | 0 | 0 |
| TBNonanes | 9 | 9 | 3 | 3 | 0 | 0 | 0 | 0 | 0 | 0 | 0 | 0 |
| MBNonanes | 9 | 9 | 4 | 5 | 0 | 0 | 0 | 0 | 0 | 0 | 0 | 0 |
| Decane | 10 | 10 | 0 | 0 | 0 | 0 | 0 | 0 | 0 | 0 | 0 | 0 |
| SBDecanes | 10 | 10 | 1 | 1 | 0 | 0 | 0 | 0 | 0 | 0 | 0 | 0 |
| DBDecanes | 10 | 10 | 2 | 2 | 0 | 0 | 0 | 0 | 0 | 0 | 0 | 0 |
| TBDecanes | 10 | 10 | 3 | 3 | 0 | 0 | 0 | 0 | 0 | 0 | 0 | 0 |
| MBDecanes | 10 | 10 | 4 | 6 | 0 | 0 | 0 | 0 | 0 | 0 | 0 | 0 |
| Undecane | 11 | 11 | 0 | 0 | 0 | 0 | 0 | 0 | 0 | 0 | 0 | 0 |
| SBUndecanes | 11 | 11 | 1 | 1 | 0 | 0 | 0 | 0 | 0 | 0 | 0 | 0 |
| DBUndecanes | 11 | 11 | 2 | 2 | 0 | 0 | 0 | 0 | 0 | 0 | 0 | 0 |
| TBUndecanes | 11 | 11 | 3 | 3 | 0 | 0 | 0 | 0 | 0 | 0 | 0 | 0 |
| MBUndecanes | 11 | 11 | 4 | 6 | 0 | 0 | 0 | 0 | 0 | 0 | 0 | 0 |
| Dodecane | 12 | 12 | 0 | 0 | 0 | 0 | 0 | 0 | 0 | 0 | 0 | 0 |
| SBDodecane | 12 | 12 | 1 | 1 | 0 | 0 | 0 | 0 | 0 | 0 | 0 | 0 |
| DBDodecane | 12 | 12 | 2 | 2 | 0 | 0 | 0 | 0 | 0 | 0 | 0 | 0 |
| TBDodecane | 12 | 12 | 3 | 3 | 0 | 0 | 0 | 0 | 0 | 0 | 0 | 0 |

TABLE 5-continued

Kerosene composition from pure and compound species definitions

| | | | | | | | | | | | | |
|---|---|---|---|---|---|---|---|---|---|---|---|---|
| MBDodecanes | 12 | 12 | 4 | 7 | 0 | 0 | 0 | 0 | 0 | 0 | 0 | 0 |
| Tridecane | 13 | 13 | 0 | 0 | 0 | 0 | 0 | 0 | 0 | 0 | 0 | 0 |
| SBTridecane | 13 | 13 | 1 | 1 | 0 | 0 | 0 | 0 | 0 | 0 | 0 | 0 |
| DBTridecane | 13 | 13 | 2 | 2 | 0 | 0 | 0 | 0 | 0 | 0 | 0 | 0 |
| TBTridecane | 13 | 13 | 3 | 3 | 0 | 0 | 0 | 0 | 0 | 0 | 0 | 0 |
| MBTridecane | 13 | 13 | 4 | 8 | 0 | 0 | 0 | 0 | 0 | 0 | 0 | 0 |
| Tetradecane | 14 | 14 | 0 | 0 | 0 | 0 | 0 | 0 | 0 | 0 | 0 | 0 |
| SBTetradecane | 14 | 14 | 1 | 1 | 0 | 0 | 0 | 0 | 0 | 0 | 0 | 0 |
| DBTetradecane | 14 | 14 | 2 | 2 | 0 | 0 | 0 | 0 | 0 | 0 | 0 | 0 |
| TBTetradecane | 14 | 14 | 3 | 3 | 0 | 0 | 0 | 0 | 0 | 0 | 0 | 0 |
| MBTetradecane | 14 | 14 | 4 | 8 | 0 | 0 | 0 | 0 | 0 | 0 | 0 | 0 |
| Pentadecane | 15 | 15 | 0 | 0 | 0 | 0 | 0 | 0 | 0 | 0 | 0 | 0 |
| SBPentadecane | 15 | 15 | 1 | 1 | 0 | 0 | 0 | 0 | 0 | 0 | 0 | 0 |
| DBPentadecane | 15 | 15 | 2 | 2 | 0 | 0 | 0 | 0 | 0 | 0 | 0 | 0 |
| TBPentadecane | 15 | 15 | 3 | 3 | 0 | 0 | 0 | 0 | 0 | 0 | 0 | 0 |
| MBPentadecane | 15 | 15 | 4 | 9 | 0 | 0 | 0 | 0 | 0 | 0 | 0 | 0 |
| Cyclopentane | 5 | 5 | 0 | 3 | 0 | 0 | 1 | 1 | 0 | 0 | 0 | 0 |
| Methylcyclopentane | 6 | 6 | 0 | 3 | 0 | 0 | 1 | 1 | 0 | 0 | 0 | 0 |
| Cyclohexane | 6 | 6 | 0 | 3 | 0 | 0 | 1 | 1 | 0 | 0 | 0 | 0 |
| C7Cyclopentanes | 7 | 7 | 0 | 3 | 0 | 0 | 1 | 1 | 0 | 0 | 0 | 0 |
| Methylcyclohexane | 7 | 7 | 0 | 3 | 0 | 0 | 1 | 1 | 0 | 0 | 0 | 0 |
| C8Cyclopentanes | 8 | 8 | 0 | 3 | 0 | 0 | 1 | 1 | 0 | 0 | 0 | 0 |
| C8Cyclohexanes | 8 | 8 | 0 | 3 | 0 | 0 | 1 | 1 | 0 | 0 | 0 | 0 |
| C9Cyclopentanes | 9 | 9 | 0 | 3 | 0 | 0 | 1 | 1 | 0 | 0 | 0 | 0 |
| C9Cyclohexanes | 9 | 9 | 0 | 3 | 0 | 0 | 1 | 1 | 0 | 0 | 0 | 0 |
| C10Cyclopentanes | 10 | 10 | 0 | 3 | 0 | 0 | 1 | 1 | 0 | 0 | 0 | 0 |
| C10Cyclohexanes | 10 | 10 | 0 | 3 | 0 | 0 | 1 | 1 | 0 | 0 | 0 | 0 |
| C11Cyclopentanes | 11 | 11 | 0 | 3 | 0 | 0 | 1 | 1 | 0 | 0 | 0 | 0 |
| C11Cyclohexanes | 11 | 11 | 0 | 3 | 0 | 0 | 1 | 1 | 0 | 0 | 0 | 0 |
| C12Cyclopentanes | 12 | 12 | 0 | 3 | 0 | 0 | 1 | 1 | 0 | 0 | 0 | 0 |
| C12Cyclohexanes | 12 | 12 | 0 | 3 | 0 | 0 | 1 | 1 | 0 | 0 | 0 | 0 |
| C13Cyclopentanes | 13 | 13 | 0 | 3 | 0 | 0 | 1 | 1 | 0 | 0 | 0 | 0 |
| C13Cyclohexanes | 13 | 13 | 0 | 3 | 0 | 0 | 1 | 1 | 0 | 0 | 0 | 0 |
| C14Cyclopentanes | 14 | 14 | 0 | 3 | 0 | 0 | 1 | 1 | 0 | 0 | 0 | 0 |
| C14Cyclohexanes | 14 | 14 | 0 | 3 | 0 | 0 | 1 | 1 | 0 | 0 | 0 | 0 |
| C15Cyclopentanes | 15 | 15 | 0 | 3 | 0 | 0 | 1 | 1 | 0 | 0 | 0 | 0 |
| C15Cyclohexanes | 15 | 15 | 0 | 3 | 0 | 0 | 1 | 1 | 0 | 0 | 0 | 0 |
| C10Decalins | 10 | 10 | 0 | 3 | 0 | 0 | 1 | 1 | 0 | 0 | 0 | 0 |
| C11Decalins | 11 | 11 | 0 | 3 | 0 | 0 | 1 | 1 | 0 | 0 | 0 | 0 |
| C12Decalins | 12 | 12 | 0 | 3 | 0 | 0 | 1 | 1 | 0 | 0 | 0 | 0 |
| C13Decalins | 13 | 13 | 0 | 3 | 0 | 0 | 1 | 1 | 0 | 0 | 0 | 0 |
| C14Decalins | 14 | 14 | 0 | 3 | 0 | 0 | 1 | 1 | 0 | 0 | 0 | 0 |
| C15Decalins | 15 | 15 | 0 | 3 | 0 | 0 | 1 | 1 | 0 | 0 | 0 | 0 |
| C8Cyclopentanes(Di-) | 8 | 8 | 0 | 3 | 0 | 0 | 1 | 1 | 0 | 0 | 0 | 0 |
| C9Cyclopentanes(Di-) | 9 | 9 | 0 | 3 | 0 | 0 | 1 | 1 | 0 | 0 | 0 | 0 |
| C10Cyclopentanes(Di-) | 10 | 10 | 0 | 3 | 0 | 0 | 1 | 1 | 0 | 0 | 0 | 0 |
| C11Cyclopentanes(Di-) | 11 | 11 | 0 | 3 | 0 | 0 | 1 | 1 | 0 | 0 | 0 | 0 |
| C12Cyclopentanes(Di-) | 12 | 12 | 0 | 3 | 0 | 0 | 1 | 1 | 0 | 0 | 0 | 0 |
| C13Cyclopentanes(Di-) | 13 | 13 | 0 | 3 | 0 | 0 | 1 | 1 | 0 | 0 | 0 | 0 |
| C14Cyclopentanes(Di-) | 14 | 14 | 0 | 3 | 0 | 0 | 1 | 1 | 0 | 0 | 0 | 0 |
| C15Cyclopentanes(Di-) | 15 | 15 | 0 | 3 | 0 | 0 | 1 | 1 | 0 | 0 | 0 | 0 |
| C9CyclohexaneIndanes | 9 | 9 | 0 | 3 | 0 | 0 | 1 | 1 | 0 | 0 | 0 | 0 |
| C10CyclohexaneIndanes | 10 | 10 | 0 | 3 | 0 | 0 | 1 | 1 | 0 | 0 | 0 | 0 |
| C11CyclohexaneIndanes | 11 | 11 | 0 | 3 | 0 | 0 | 1 | 1 | 0 | 0 | 0 | 0 |
| C12CyclohexaneIndanes | 12 | 12 | 0 | 3 | 0 | 0 | 1 | 1 | 0 | 0 | 0 | 0 |
| C13CyclohexaneIndanes | 13 | 13 | 0 | 3 | 0 | 0 | 1 | 1 | 0 | 0 | 0 | 0 |
| C14CyclohexaneIndanes | 14 | 14 | 0 | 3 | 0 | 0 | 1 | 1 | 0 | 0 | 0 | 0 |
| C15CyclohexaneIndanes | 15 | 15 | 0 | 3 | 0 | 0 | 1 | 1 | 0 | 0 | 0 | 0 |
| C10TetrahydroAromatics(Mono) | 10 | 10 | 0 | 3 | 0 | 0 | 1 | 1 | 1 | 1 | 0 | 4 |
| C11TetrahydroAromatics(Mono) | 11 | 11 | 0 | 3 | 0 | 0 | 1 | 1 | 1 | 1 | 0 | 4 |
| C12TetrahydroAromatics(Mono) | 12 | 12 | 0 | 3 | 0 | 0 | 1 | 1 | 1 | 1 | 0 | 4 |
| C13TetrahydroAromatics(Mono) | 13 | 13 | 0 | 3 | 0 | 0 | 1 | 1 | 1 | 1 | 0 | 4 |
| C14TetrahydroAromatics(Mono) | 14 | 14 | 0 | 3 | 0 | 0 | 1 | 1 | 1 | 1 | 0 | 4 |
| C15TetrahydroAromatics(Mono) | 15 | 15 | 0 | 3 | 0 | 0 | 1 | 1 | 1 | 1 | 0 | 4 |
| C10Indanes | 10 | 10 | 0 | 3 | 0 | 0 | 1 | 1 | 1 | 1 | 0 | 4 |
| C11Indanes | 11 | 11 | 0 | 3 | 0 | 0 | 1 | 1 | 1 | 1 | 0 | 4 |
| C12Indanes | 12 | 12 | 0 | 3 | 0 | 0 | 1 | 1 | 1 | 1 | 0 | 4 |
| C13Indanes | 13 | 13 | 0 | 3 | 0 | 0 | 1 | 1 | 1 | 1 | 0 | 4 |
| C14Indanes | 14 | 14 | 0 | 3 | 0 | 0 | 1 | 1 | 1 | 1 | 0 | 4 |
| C15Indanes | 15 | 15 | 0 | 3 | 0 | 0 | 1 | 1 | 1 | 1 | 0 | 4 |
| C8Aromatics | 8 | 8 | 0 | 3 | 0 | 0 | 1 | 1 | 1 | 1 | 0 | 2 |
| C9Aromatics | 9 | 9 | 0 | 3 | 0 | 0 | 1 | 1 | 1 | 1 | 0 | 3 |
| C10Aromatics(Mono) | 10 | 10 | 0 | 3 | 0 | 0 | 1 | 1 | 1 | 1 | 0 | 4 |
| C11Aromatics(Mono) | 11 | 11 | 0 | 3 | 0 | 0 | 1 | 1 | 1 | 1 | 0 | 4 |
| C12Aromatics(Mono) | 12 | 12 | 0 | 3 | 0 | 0 | 1 | 1 | 1 | 1 | 0 | 4 |
| C13Aromatics(Mono) | 13 | 13 | 0 | 3 | 0 | 0 | 1 | 1 | 1 | 1 | 0 | 4 |
| C14Aromatics(Mono) | 14 | 14 | 0 | 3 | 0 | 0 | 1 | 1 | 1 | 1 | 0 | 4 |
| C15Aromatics(Mono) | 15 | 15 | 0 | 3 | 0 | 0 | 1 | 1 | 1 | 1 | 0 | 4 |

TABLE 5-continued

Kerosene composition from pure and compound species definitions

| | | | | | | | | | | | | |
|---|---|---|---|---|---|---|---|---|---|---|---|---|
| C10Aromatics(Di-) | 10 | 10 | 0 | 3 | 0 | 0 | 1 | 1 | 2 | 2 | 0 | 4 |
| C11Aromatics(Di-) | 11 | 11 | 0 | 3 | 0 | 0 | 1 | 1 | 2 | 2 | 0 | 4 |
| C12Aromatics(Di-) | 12 | 12 | 0 | 3 | 0 | 0 | 1 | 1 | 2 | 2 | 0 | 4 |
| C13Aromatics(Di-) | 13 | 13 | 0 | 3 | 0 | 0 | 1 | 1 | 2 | 2 | 0 | 4 |
| C14Aromatics(Di-) | 14 | 14 | 0 | 3 | 0 | 0 | 1 | 1 | 2 | 2 | 0 | 4 |
| C15Aromatics(Di-) | 15 | 15 | 0 | 3 | 0 | 0 | 1 | 1 | 2 | 2 | 0 | 4 |
| C12Biphenyls | 12 | 12 | 0 | 3 | 0 | 0 | 2 | 2 | 2 | 2 | 0 | 4 |
| C13Biphenyls | 13 | 13 | 0 | 3 | 0 | 0 | 2 | 2 | 2 | 2 | 0 | 4 |
| C14Biphenyls | 14 | 14 | 0 | 3 | 0 | 0 | 2 | 2 | 2 | 2 | 0 | 4 |
| C15Biphenyls | 15 | 15 | 0 | 3 | 0 | 0 | 2 | 2 | 2 | 2 | 0 | 4 |
| C12Hexahydro-biphenyls | 12 | 12 | 0 | 3 | 0 | 0 | 2 | 2 | 1 | 1 | 0 | 4 |
| C13Hexahydro-biphenyls | 13 | 13 | 0 | 3 | 0 | 0 | 2 | 2 | 1 | 1 | 0 | 4 |
| C14Hexahydro-biphenyls | 14 | 14 | 0 | 3 | 0 | 0 | 2 | 2 | 1 | 1 | 0 | 4 |
| C15Hexahydro-biphenyls | 15 | 15 | 0 | 3 | 0 | 0 | 2 | 2 | 1 | 1 | 0 | 4 |

| | Structural Characteristics: | | | | | | | |
|---|---|---|---|---|---|---|---|---|
| | 5-Carbon Rings | | 6-Carbon Rings | | Cycloalkane Substituents | | | Composition |
| Species | Min | Max | Min | Max | Min | Max | Pure Species | molar |
| Octane | 0 | 0 | 0 | 0 | 0 | 0 | 1 | 0.0000 |
| SBOctanes | 0 | 0 | 0 | 0 | 0 | 0 | 1 | 0.0000 |
| DBOctanes | 0 | 0 | 0 | 0 | 0 | 0 | 2 | 0.0000 |
| TBOctanes | 0 | 0 | 0 | 0 | 0 | 0 | 2 | 0.0000 |
| MBOctanes | 0 | 0 | 0 | 0 | 0 | 0 | 1 | 0.0000 |
| Nonane | 0 | 0 | 0 | 0 | 0 | 0 | 1 | 0.0000 |
| SBNonanes | 0 | 0 | 0 | 0 | 0 | 0 | 1 | 0.0000 |
| DBNonanes | 0 | 0 | 0 | 0 | 0 | 0 | 2 | 0.0000 |
| TBNonanes | 0 | 0 | 0 | 0 | 0 | 0 | 2 | 0.0000 |
| MBNonanes | 0 | 0 | 0 | 0 | 0 | 0 | 2 | 0.0000 |
| Decane | 0 | 0 | 0 | 0 | 0 | 0 | 1 | 0.0000 |
| SBDecanes | 0 | 0 | 0 | 0 | 0 | 0 | 1 | 0.0000 |
| DBDecanes | 0 | 0 | 0 | 0 | 0 | 0 | 2 | 0.0000 |
| TBDecanes | 0 | 0 | 0 | 0 | 0 | 0 | 2 | 0.0000 |
| MBDecanes | 0 | 0 | 0 | 0 | 0 | 0 | 3 | 0.0000 |
| Undecane | 0 | 0 | 0 | 0 | 0 | 0 | 1 | 0.0000 |
| SBUndecanes | 0 | 0 | 0 | 0 | 0 | 0 | 1 | 0.0000 |
| DBUndecanes | 0 | 0 | 0 | 0 | 0 | 0 | 2 | 0.0000 |
| TBUndecanes | 0 | 0 | 0 | 0 | 0 | 0 | 2 | 0.0000 |
| MBUndecanes | 0 | 0 | 0 | 0 | 0 | 0 | 3 | 0.0000 |
| Dodecane | 0 | 0 | 0 | 0 | 0 | 0 | 1 | 0.0810 |
| SBDodecane | 0 | 0 | 0 | 0 | 0 | 0 | 1 | 0.0000 |
| DBDodecane | 0 | 0 | 0 | 0 | 0 | 0 | 2 | 0.0000 |
| TBDodecane | 0 | 0 | 0 | 0 | 0 | 0 | 2 | 0.0000 |
| MBDodecanes | 0 | 0 | 0 | 0 | 0 | 0 | 3 | 0.0000 |
| Tridecane | 0 | 0 | 0 | 0 | 0 | 0 | 1 | 0.2280 |
| SBTridecane | 0 | 0 | 0 | 0 | 0 | 0 | 1 | 0.0000 |
| DBTridecane | 0 | 0 | 0 | 0 | 0 | 0 | 2 | 0.0000 |
| TBTridecane | 0 | 0 | 0 | 0 | 0 | 0 | 2 | 0.0000 |
| MBTridecane | 0 | 0 | 0 | 0 | 0 | 0 | 3 | 0.0000 |
| Tetradecane | 0 | 0 | 0 | 0 | 0 | 0 | 1 | 0.0194 |
| SBTetradecane | 0 | 0 | 0 | 0 | 0 | 0 | 1 | 0.0000 |
| DBTetradecane | 0 | 0 | 0 | 0 | 0 | 0 | 2 | 0.0000 |
| TBTetradecane | 0 | 0 | 0 | 0 | 0 | 0 | 2 | 0.0000 |
| MBTetradecane | 0 | 0 | 0 | 0 | 0 | 0 | 3 | 0.0000 |
| Pentadecane | 0 | 0 | 0 | 0 | 0 | 0 | 1 | 0.0000 |
| SBPentadecane | 0 | 0 | 0 | 0 | 0 | 0 | 1 | 0.0000 |
| DBPentadecane | 0 | 0 | 0 | 0 | 0 | 0 | 2 | 0.0000 |
| TBPentadecane | 0 | 0 | 0 | 0 | 0 | 0 | 2 | 0.0000 |
| MBPentadecane | 0 | 0 | 0 | 0 | 0 | 0 | 3 | 0.0000 |
| Cyclopentane | 1 | 1 | 0 | 0 | 0 | 0 | 1 | 0.0000 |
| Methylcyclopentane | 1 | 1 | 0 | 0 | 0 | 1 | 1 | 0.0000 |
| Cyclohexane | 0 | 0 | 1 | 1 | 0 | 0 | 1 | 0.0000 |
| C7Cyclopentanes | 1 | 1 | 0 | 0 | 0 | 2 | 3 | 0.0000 |
| Methylcyclohexane | 0 | 0 | 1 | 1 | 0 | 1 | 1 | 0.0000 |
| C8Cyclopentanes | 1 | 1 | 0 | 0 | 0 | 3 | 6 | 0.0000 |
| C8Cyclohexanes | 0 | 0 | 1 | 1 | 0 | 2 | 3 | 0.0000 |
| C9Cyclopentanes | 1 | 1 | 0 | 0 | 0 | 4 | 12 | 0.0000 |
| C9Cyclohexanes | 0 | 0 | 1 | 1 | 0 | 3 | 6 | 0.0000 |
| C10Cyclopentanes | 1 | 1 | 0 | 0 | 0 | 4 | 17 | 0.0000 |
| C10Cyclohexanes | 0 | 0 | 1 | 1 | 0 | 4 | 12 | 0.0000 |
| C11Cyclopentanes | 1 | 1 | 0 | 0 | 0 | 4 | 25 | 0.0000 |
| C11Cyclohexanes | 0 | 0 | 1 | 1 | 0 | 4 | 17 | 0.0000 |
| C12Cyclopentanes | 1 | 1 | 0 | 0 | 0 | 4 | 33 | 0.0000 |
| C12Cyclohexanes | 0 | 0 | 1 | 1 | 0 | 4 | 25 | 0.2050 |
| C13Cyclopentanes | 1 | 1 | 0 | 0 | 0 | 4 | 40 | 0.0000 |
| C13Cyclohexanes | 0 | 0 | 1 | 1 | 0 | 4 | 33 | 0.0000 |

TABLE 5-continued

Kerosene composition from pure and compound species definitions

| | | | | | | | | |
|---|---|---|---|---|---|---|---|---|
| C14Cyclopentanes | 1 | 1 | 0 | 0 | 0 | 4 | 45 | 0.0000 |
| C14Cyclohexanes | 0 | 0 | 1 | 1 | 0 | 4 | 40 | 0.0000 |
| C15Cyclopentanes | 1 | 1 | 0 | 0 | 0 | 4 | 48 | 0.0000 |
| C15Cyclohexanes | 0 | 0 | 1 | 1 | 0 | 4 | 45 | 0.0000 |
| C10Decalins | 0 | 0 | 2 | 2 | 0 | 4 | 1 | 0.0000 |
| C11Decalins | 0 | 0 | 2 | 2 | 0 | 4 | 1 | 0.0000 |
| C12Decalins | 0 | 0 | 2 | 2 | 0 | 4 | 3 | 0.0000 |
| C13Decalins | 0 | 0 | 2 | 2 | 0 | 4 | 6 | 0.0000 |
| C14Decalins | 0 | 0 | 2 | 2 | 0 | 4 | 12 | 0.0000 |
| C15Decalins | 0 | 0 | 2 | 2 | 0 | 4 | 17 | 0.0000 |
| C8Cyclopentanes(Di-) | 2 | 2 | 0 | 0 | 0 | 4 | 1 | 0.0000 |
| C9Cyclopentanes(Di-) | 2 | 2 | 0 | 0 | 0 | 4 | 1 | 0.0000 |
| C10Cyclopentanes(Di-) | 2 | 2 | 0 | 0 | 0 | 4 | 3 | 0.0000 |
| C11Cyclopentanes(Di-) | 2 | 2 | 0 | 0 | 0 | 4 | 6 | 0.0000 |
| C12Cyclopentanes(Di-) | 2 | 2 | 0 | 0 | 0 | 4 | 12 | 0.0000 |
| C13Cyclopentanes(Di-) | 2 | 2 | 0 | 0 | 0 | 4 | 17 | 0.0000 |
| C14Cyclopentanes(Di-) | 2 | 2 | 0 | 0 | 0 | 4 | 25 | 0.0000 |
| C15Cyclopentanes(Di-) | 2 | 2 | 0 | 0 | 0 | 4 | 33 | 0.0000 |
| C9CyclohexaneIndanes | 1 | 1 | 1 | 1 | 0 | 4 | 1 | 0.0000 |
| C10CyclohexaneIndanes | 1 | 1 | 1 | 1 | 0 | 4 | 1 | 0.0000 |
| C11CyclohexaneIndanes | 1 | 1 | 1 | 1 | 0 | 4 | 3 | 0.0000 |
| C12CyclohexaneIndanes | 1 | 1 | 1 | 1 | 0 | 4 | 6 | 0.0000 |
| C13CyclohexaneIndanes | 1 | 1 | 1 | 1 | 0 | 4 | 12 | 0.2496 |
| C14CyclohexaneIndanes | 1 | 1 | 1 | 1 | 0 | 4 | 17 | 0.0000 |
| C15CyclohexaneIndanes | 1 | 1 | 1 | 1 | 0 | 4 | 25 | 0.0000 |
| C10TetrahydroAromatics(Mono) | 0 | 0 | 1 | 1 | 0 | 4 | 1 | 0.0000 |
| C11TetrahydroAromatics(Mono) | 0 | 0 | 1 | 1 | 0 | 4 | 2 | 0.0000 |
| C12TetrahydroAromatics(Mono) | 0 | 0 | 1 | 1 | 0 | 4 | 5 | 0.0000 |
| C13TetrahydroAromatics(Mono) | 0 | 0 | 1 | 1 | 0 | 4 | 10 | 0.0000 |
| C14TetrahydroAromatics(Mono) | 0 | 0 | 1 | 1 | 0 | 4 | 19 | 0.0000 |
| C15TetrahydroAromatics(Mono) | 0 | 0 | 1 | 1 | 0 | 4 | 27 | 0.0000 |
| C10Indanes | 1 | 1 | 0 | 0 | 0 | 4 | 2 | 0.0000 |
| C11Indanes | 1 | 1 | 0 | 0 | 0 | 4 | 5 | 0.0000 |
| C12Indanes | 1 | 1 | 0 | 0 | 0 | 4 | 10 | 0.0273 |
| C13Indanes | 1 | 1 | 0 | 0 | 0 | 4 | 18 | 0.0000 |
| C14Indanes | 1 | 1 | 0 | 0 | 0 | 4 | 26 | 0.0000 |
| C15Indanes | 1 | 1 | 0 | 0 | 0 | 4 | 37 | 0.0000 |
| C8Aromatics | 0 | 0 | 0 | 0 | 0 | 0 | 2 | 0.0000 |
| C9Aromatics | 0 | 0 | 0 | 0 | 0 | 0 | 4 | 0.0000 |
| C10Aromatics(Mono) | 0 | 0 | 0 | 0 | 0 | 0 | 7 | 0.0000 |
| C11Aromatics(Mono) | 0 | 0 | 0 | 0 | 0 | 0 | 10 | 0.0000 |
| C12Aromatics(Mono) | 0 | 0 | 0 | 0 | 0 | 0 | 14 | 0.0000 |
| C13Aromatics(Mono) | 0 | 0 | 0 | 0 | 0 | 0 | 18 | 0.1897 |
| C14Aromatics(Mono) | 0 | 0 | 0 | 0 | 0 | 0 | 21 | 0.0000 |
| C15Aromatics(Mono) | 0 | 0 | 0 | 0 | 0 | 0 | 23 | 0.0000 |
| C10Aromatics(Di-) | 0 | 0 | 0 | 0 | 0 | 0 | 1 | 0.0000 |
| C11Aromatics(Di-) | 0 | 0 | 0 | 0 | 0 | 0 | 1 | 0.0000 |
| C12Aromatics(Di-) | 0 | 0 | 0 | 0 | 0 | 0 | 2 | 0.0000 |
| C13Aromatics(Di-) | 0 | 0 | 0 | 0 | 0 | 0 | 4 | 0.0000 |
| C14Aromatics(Di-) | 0 | 0 | 0 | 0 | 0 | 0 | 7 | 0.0000 |
| C15Aromatics(Di-) | 0 | 0 | 0 | 0 | 0 | 0 | 10 | 0.0000 |
| C12Biphenyls | 0 | 0 | 0 | 0 | 0 | 0 | 1 | 0.0000 |
| C13Biphenyls | 0 | 0 | 0 | 0 | 0 | 0 | 2 | 0.0000 |
| C14Biphenyls | 0 | 0 | 0 | 0 | 0 | 0 | 3 | 0.0000 |
| C15Biphenyls | 0 | 0 | 0 | 0 | 0 | 0 | 5 | 0.0000 |
| C12Hexahydro-biphenyls | 0 | 0 | 1 | 1 | 0 | 4 | 1 | 0.0000 |
| C13Hexahydro-biphenyls | 0 | 0 | 1 | 1 | 0 | 4 | 4 | 0.0000 |
| C14Hexahydro-biphenyls | 0 | 0 | 1 | 1 | 0 | 4 | 7 | 0.0000 |
| C15Hexahydro-biphenyls | 0 | 0 | 1 | 1 | 0 | 4 | 15 | 0.0000 |

Once the reduction in the number of species to 116 without a significant sacrifice in accuracy is achieved, a problem remains in estimating the composition of the kerosene sample (Table 1) in terms of the mixture components (Table 5). Such inference is accomplished by determining the composition ($X_i$) that maximizes the Shannon entropy of the mixture (S) (Equation 1) and satisfies the constraints imposed by the application of mixing rules (Equation 2) in the calculation of the properties of the mixture to match the average properties of the sample ($P_j$).

$$\max_X \left\{ S = -\sum_i X_i \cdot \text{Ln}(X_i) \right\} \quad (1)$$

$$\overline{P}_j = \sum_j X_i \cdot P_{i,j} \quad (2)$$

The estimated composition for the kerosene sample in Table 1 is reported in the last column of Table 5. The reconstruction of the kerosene sample by applying the mixing rules (Equation 2) is shown in Table 6.

TABLE 6

Kerosene sample reconstruction

| Analysis | Measured | Reconstructed |
|---|---|---|
| Specific Gravity | 0.81 | 0.86 |
| Molecular Weight | 170 | 177 |
| Hydrogen Content, wt % | 0.138 | 0.138 |
| Aromatics, vol % | 20.0 | 20.4 |
| Olefins, vol % | <0.1 | 0.0 |
| ASTM D86, vol %/° C. | | |
| IBP | 174 | 177 |
| 10% | 205 | 206 |
| 30% | 218 | 223 |
| 50% | 232 | 224 |
| 70% | 245 | 232 |
| 90% | 258 | 262 |
| FBP | 300 | 264 |

The reconstructed sample shows a good agreement with the measured values. The decreasing accuracy of the estimated boiling temperatures with the proximity of the final boiling point are the consequence of increasing deviations with carbon number in the estimation of the boiling temperatures of pure species by Joback.

In cases where a detailed composition of the sample is required in a simulation (e.g. chemical reactor unit operation), the molar fraction ($Z_j$) of every pure species (j) in a compound species (i) is calculated from the molar fraction ($X_i$) of the compound species (i) by breaking it down back into their components in equilibrium as formulated in equation (3). The only information required to execute this calculation is the Gibbs free energy of formation of the pure species at the reference temperature (Equation 4). In the present example, it the equation is used to calculate the composition of the kerosene sample in terms of 1010 pure species.

$$X_i = Z_j \left\{ 1 + \sum_{k \neq j} K_{k,j} \right\} \quad (3)$$

$$K_{k,j} = \exp\left\{ -\frac{G_k - G_j}{RT} \right\} \quad (4)$$

Example 2

Extended Application

The previous example illustrated the most basic application of the complex mixture modeling algorithm for the characterization of petroleum fractions. Within a commercial chemical process model, the algorithm enables the application of detailed kinetics and fundamental reactor models while keeping the number of species manageable. Moreover, it permits the creation of interfaces to go from petroleum fractions towards mixtures of pure and compound species to feed reactor models and then back to oil fractions.

The solution of equations (1) and (2) yields a composition that maximizes the Shannon Entropy of the mixture. However, this solution is not unique as any other composition that satisfies the constraints in equation (2) might also be valid and even approach closer to the real composition of the sample.

Consequently, in order to evaluate the performance of the algorithm of the process of the invention in estimating the compositions of the oil fractions, estimated compositions for a database of 50 naphtha samples were compared against experimental measurements. The database contains not only properties for every oil fraction such as specific gravity, molecular weight and boiling point curve, but also measured compositions of every sample from gas chromatography.

Figure 2:
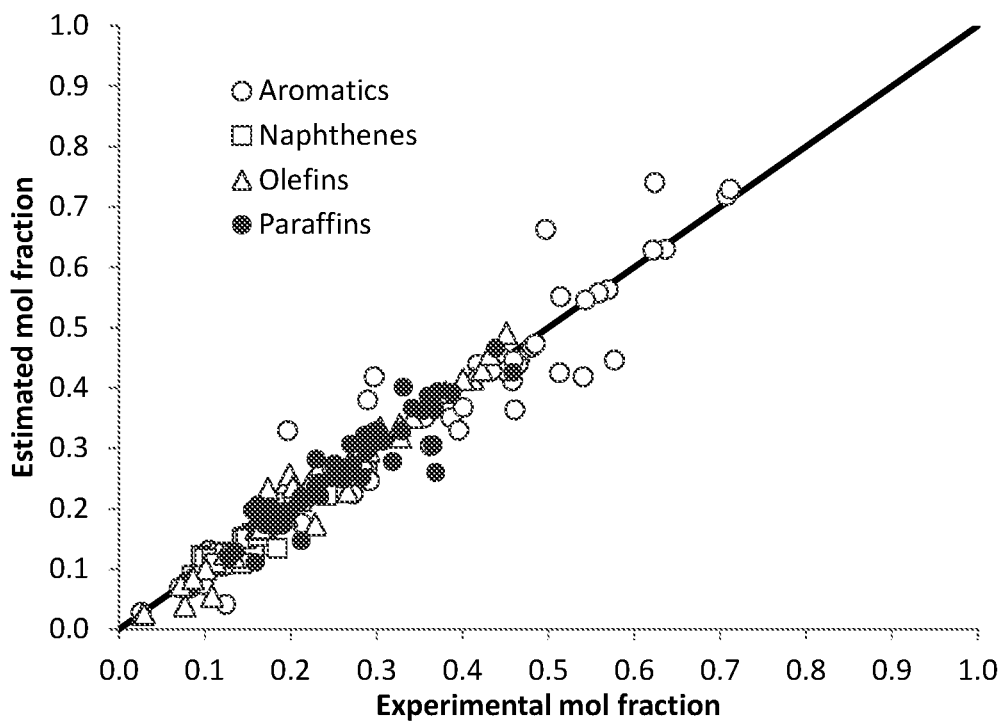
FIG. 2 is a graphical representation the results of a comparison of composition results from an embodiment of the invention with analytical results.

In this example, a species base comprising 235 molecules matching those previously identified in a gas chromatographic analysis was used. Furthermore, this base is grouped into a mixture of 68 species (47 compound species) that describes a naphtha cut. The results are presented in FIG. 2 in the form of parity plot for the overall composition in terms of hydrocarbon families.

This example illustrates the capability of the process of the invention to accurately model the composition of naphtha fractions and provide suitable composition information for further process simulation processes.

In another aspect the invention includes assembling a compilation of hydrocarbon compounds and compound species (as defined below) that includes all compounds and compound species that will be useful for a desired purpose (such as petroleum refining), selecting from the assembly the compounds and compound species and their physical and chemical properties that may be included in a given hydrocarbon mixture, and calculating a composition that is consistent with available analytical information for the mixture.

Applicants developed an alternative, deterministic approach to molecular reconstruction to generate the new compilation. The approach replaces the stochastic methods with means to select from molecules from a molecular database that contains all chemical constituents and their isomers within a set of constraints tailored to capture petroleum hydrocarbon fractions of interest. Rather than build the database when needed to model a sample, applicants prepare a comprehensive database a priori, from which appropriate compound species and their respective physical and chemical properties, may be selected when needed to match a given sample for which the composition and properties are to be calculated (as representative of the actual molecular composition).

In general the database will contain hydrocarbon species with carbon numbers likely to be of interest. Carbon species up to about $C_{40}$ is adequate for most purposes since petroleum hydrocarbon species above $C_{40}$ are generally asphaltenes for which detailed individual species identification is impossible and of little process interest.

The method used by Applicants is dependent on two competing factors, the completeness of the database and the size of the database. Unfortunately, most gasoil reconstructions require representations of up to 40 atoms in a hydrogen suppressed molecular isomer which requires the creation of a database in size beyond the scope of the current state-of-the-art graph generate-and-test algorithms, such as those described by Pieroncely et al. (2012)(Julio E Peironcely, Miguel Rojas-Chertó, Davide Fichera4, Theo Reijmers, Leon Coulier, Jean-Loup Faulon and Thomas Hankemeier; *OMG: Open Molecule Generator*; Journal of Cheminformatics 2012, 4:21; http://www.jcheminf.com/content/4/1/21).

A higher carbon number hydrocarbon is even more difficult to create. As a result, a hybrid, two stage method consisting of colored canonical graphs is used. Colored canonical graphs are representations of molecules consisting of extended Joback groups as the colors and the connectivity between all of the extended Joback groups in each molecule as the canonical graphs. Colored graphs are chosen to maximize computational speed during database construction and CPS run-time.

In another aspect the representative mixture as calculated in the as described above is expanded to the individual compounds in the mixture. In effect it is a reversal of the determination of the compound species used in the first two embodiments. This is desirable when the mixture is to be used in chemical reaction simulation since the simulation will be far more accurate with specific compounds. While the consolidation of compound species is highly desirable to provide workable number of component, for chemical reaction simulations it cannot be presumed that the groups (compound species) will behave alike. Thus, the calculated representative mixture is expanded by searching for all molecules in the colored graph database represented by each compound species. The resulting expanded hydrocarbon representative mixture the composition is then easily calculated by multiplying the percentage of the compound species in the unexpanded mixture by the equilibrium mixture percentage of the individual compounds.

The first set of embodiments of the invention is a software system that improves the operation, adequacy and efficiency of a computer system that is programmed to calculate, inter alia, operating parameters and results of hydrocarbon processing units by providing an additional program (herein termed Oil Speciation programs as described comprising a method of estimating and consolidating molecular composition components and properties of hydrocarbon mixtures such as petroleum fractions. Exemplary of the addition Oil Speciation program to the above described computer systems one that is capable of calculating a calculated hydrocarbon mixture obtained from predetermined analytical data comprising;
  a) providing a compilation of identified chemical pure or compound species for which a Shannon entropy may be calculated marked with identifiers and including chemical and physical properties, wherein compound species comprise a compilation of related molecules in chemical equilibrium, wherein the compound species chemical and physical properties are computed by group contribution methods, and wherein the composition of each pure or compound species in the hydrocarbon mixture that maximizes a Shannon entropy of the compilation is calculated by determining the composition $(X_i)$ of each compound or compound species that maximizes the Shannon entropy of the mixture, S, by a model that satisfies the equation and satisfies the constraints imposed by the application of mixing rules by the equation $$\overline{P}_j = \sum_j X_i \cdot P_{i,j}$$

and calculating of the properties of the mixture to match the average properties of a sample hydrocarbon mixture, $P_j$;
  b) providing average analytical properties of a hydrocarbon mixture;
  c) selecting pure and compound species for a specific hydrocarbon mixture of interest;
  d) determining a composition of each pure or compound species in the hydrocarbon mixture having a Shannon entropy that maximizes the Shannon entropy of the hydrocarbon mixture and satisfies constraints imposed by the application of mixing rules;
  e) calculating properties of the hydrocarbon mixture that match the average analytical properties of the hydrocarbon mixture to produce calculated results; and
  f) arranging the calculated results of step e) a in a tangible, non-transitory database and utilizing the database in the operation of the computerized programmed to calculate operating parameters and results of hydrocarbon processing units.

The Oil Speciation program(s) may also include calculations of the compound species of step a) by a combination of group contribution and molecular connectivity methods and in some aspects hydrocarbon mixtures having carbon numbers of 1 to 40.

The computer system so configured is more efficient and more accurate than a system without the added Oil Speciation calculation. If the system must only operate on bulk, conventional analytical data such as distillation boiling range curve(s), chromatographic analysis (for chemical families such as paraffins, olefins, naphthenes and aromatics) and Mass Spectrometry analysis the resulting computer system operation will produce less accurate results. If, on the other hand if a complete detailed analysis of the chemical compound in the petroleum fraction could be known and used in the program the system would require much longer computer operating time to product results that would be little more accurate than when using the Oil Speciation program. Suitable programs that are capable of calculating, inter alia, operating parameters and results of hydrocarbon processing units include ProMax™, Aspen Plus and HYSYS™.

The second set of embodiments of the invention are methods for control of petroleum refinery processes by using calculated operating parameters to set actual operating parameters to change results of actual operations. Exemplary of such method(s) are a process that utilize a computer system for calculating operating parameters for operating a refinery process for separation or conversion of components of petroleum fractions or hydrocarbon mixtures comprising;
  a) selecting operating parameters of temperature, pressure and feedstock input flow rate, and analysis data for the petroleum fraction or hydrocarbon feed to be used in the petroleum refining operation and entering the operating parameters and petroleum analytical data into a computer implemented process simulation software program;
  b) entering into the computer implemented program, a computer implemented subprogram for characterizing compounds in a hydrocarbon mixture comprising;
    1) providing compilation of identified chemical pure or compound species marked with identifiers and including chemical and physical properties, wherein compound species comprise a compilation of isomeric molecules in chemical equilibrium and wherein the compound species' chemical and physical properties are computed by group contribution methods;
    2) providing measured analytical properties of a hydrocarbon mixture;
    3) selecting pure and compound species for a specific hydrocarbon mixture of interest;
    4) determining a composition of each pure or compound species in the hydrocarbon mixture that maximizes Shannon entropy of the specific mixture and satisfies constraints imposed by application of mixing rules;
  c) operating the computer implemented process simulation software program with the subprogram step of 1(a) to calculate certain properties of the petroleum fraction or hydrocarbon mixture feedstock selected for the petroleum fraction or hydrocarbon mixture from the analytical data of step a) that match the average analytical properties of the hydrocarbon mixture;

d) running the process simulation program using the calculated properties of the petroleum fraction or hydrocarbon mixture of step b) with various selected operating parameters until a desired process result or performance is obtained by the calculations of the simulation program;

e) selecting those operating parameters of step c) that were used to obtain the desired result or performance and entering them into the operating system of the refinery process for separation or conversion of components of a petroleum fraction or hydrocarbon mixture;

wherein the computer subprogram comprises those that are capable of calculating a calculated hydrocarbon mixture obtained from predetermined analytical data comprising:

a) providing a compilation of identified chemical pure or compound species for which a Shannon entropy may be calculated marked with identifiers and including chemical and physical properties, wherein compound species comprise a compilation of related molecules in chemical equilibrium, wherein the compound species chemical and physical properties are computed by group contribution methods, and wherein the composition of each pure or compound species in the hydrocarbon mixture that maximizes a Shannon entropy of the compilation is calculated by determining the composition ($X_i$) of each compound or compound species that maximizes the Shannon entropy of the mixture, S, by a model that satisfies the equation $$\max_X \left\{ S = -\sum_i X_i \cdot \text{Ln}(X_i) \right\}$$

and satisfies the constraints imposed by the application of mixing rules by the equation $$\overline{P}_j = \sum_j X_i \cdot P_{i,j}$$

and calculating of the properties of the mixture to match the average properties of a sample hydrocarbon mixture, $P_j$;

b) providing average analytical properties of a hydrocarbon mixture;

c) selecting pure and compound species for a specific hydrocarbon mixture of interest;

d) determining a composition of each pure or compound species in the hydrocarbon mixture having a Shannon entropy that maximizes the Shannon entropy of the hydrocarbon mixture and satisfies constraints imposed by the application of mixing rules;

e) calculating properties of the hydrocarbon mixture that match the average analytical properties of the hydrocarbon mixture to produce calculated results; and f) arranging the calculated results of step e) a in a tangible, non-transitory database and utilizing the database in the operation of the computerized programmed to calculate operating parameters and results of hydrocarbon processing units.

As in the first w embodiments the Oil Speciation program(s) may also include calculation of the compound species of step a) by a combination of group contribution and molecular connectivity methods and in some aspects include hydrocarbons having carbon numbers of 1 to 40.

Refinery processes as used herein include distillation units, steam cracking units, pyrolysis, steam reforming units, catalytic cracking units, hydrocracking unit, catalytic reforming units, isomeration units, desulfuration units and other units known to those skilled in the petroleum refining arts. Operating parameters include, inter alia, liquid and gas flow rates, temperature and pressure. These are generally controlled by automated control valves and other means. For example, the temperature of a distillation unit may be controlled by heating the input stream with a steam heated heat exchanger, the heat capacity and temperature which may, in turn, be controlled by the flow rate of steam to the exchanger. The flow rate of the input stream to the distillation unit may be controlled by automated control valve(s) and the pressure in the unit controlled by valves on the outlet streams. pressure The third set of embodiments of the invention comprise article(s) of manufacture consisting of a software program (termed here Oil Speciation programs) disposed on non-transitory machine readable media, which program comprises calculation of molecular composition components and properties of hydrocarbon mixtures such as petroleum fractions process steps to provide molecular grouping of complex hydrocarbon mixtures, such as a petroleum fractions (or other chemical hydrocarbon mixture) in a manner that represents the actual molecular composition in a sufficiently simplified manner for convenient utility. Machine readable non-transitory media includes computer hard drive (mechanical and solid state), flash drives, computer disks (CDs), DVDs and other media capable of storing computer instructions in a manner that can be accessed by a computer system. Exemplary of the Oil Speciation software programs are those that those that are capable of calculating a calculated hydrocarbon mixture obtained from predetermined analytical data comprising;

a) providing a compilation of identified chemical pure or compound species for which a Shannon entropy may be calculated marked with identifiers and including chemical and physical properties, wherein compound species comprise a compilation of related molecules in chemical equilibrium, wherein the compound species chemical and physical properties are computed by group contribution methods, and wherein the composition of each pure or compound species in the hydrocarbon mixture that maximizes a Shannon entropy of the compilation is calculated by determining the composition ($X_i$) of each compound or compound species that maximizes the Shannon entropy of the mixture, S, by a model that satisfies the equation $$\max_X \left\{ S = -\sum_i X_i \cdot \text{Ln}(X_i) \right\}$$

and satisfies the constraints imposed by the application of mixing rules by the equation $$\overline{P}_j = \sum_j X_i \cdot P_{i,j}$$

and calculating of the properties of the mixture to match the average properties of a sample hydrocarbon mixture, $P_j$;

b) providing average analytical properties of a hydrocarbon mixture;
c) selecting pure and compound species for a specific hydrocarbon mixture of interest;
d) determining a composition of each pure or compound species in the hydrocarbon mixture having a Shannon entropy that maximizes the Shannon entropy of the hydrocarbon mixture and satisfies constraints imposed by the application of mixing rules;
e) calculating properties of the hydrocarbon mixture that match the average analytical properties of the hydrocarbon mixture to produce calculated results; and
f) arranging the calculated results of step e) a in a tangible, non-transitory database and utilizing the database in the operation of the computerized programmed to calculate operating parameters and results of hydrocarbon processing units.

The Oil Speciation program(s) may also include calculation of the compound species of step a) by a combination of group contribution and molecular connectivity methods and in some aspects wherein the hydrocarbon mixture comprises hydrocarbons having carbon numbers of 1 to 40.

While the invention has been particularly shown and described in particular embodiments above, those skilled in the art will understand that changes in form and detail may be made without departing from the spirit and scope of the invention.

The invention claimed is:

1. A method for control of petroleum refinery processes comprising a computer system configured to calculate operating parameters for refinery processes for the separation or conversion of components of a petroleum fraction or hydrocarbon mixture and a non-transitory machine-readable program capable of calculating a calculated hydrocarbon mixture from predetermined analytical data, said second non-transitory program comprising:
   a) selecting operating parameters of temperature, pressure and feedstock input flow rate, and analysis data for the petroleum fraction or hydrocarbon feed to be used in the petroleum refining operation and entering said operating parameters and petroleum analytical data into a computer system;
   b) entering into the computer system, a computer implemented subprogram for characterizing compounds in a hydrocarbon mixture comprising:
      1) providing compilation of identified chemical pure or compound species marked with identifiers and including chemical and physical properties, wherein compound species comprise a compilation of isomeric molecules in chemical equilibrium and wherein the compound species' chemical and physical properties are computed by group contribution methods;
      2) providing measured analytical properties of a hydrocarbon mixture;
      3) selecting pure and compound species for a specific hydrocarbon mixture of interest;
      4) determining a composition of each pure or compound species in the hydrocarbon mixture that maximizes Shannon entropy of the specific mixture and satisfies constraints imposed by application of mixing rules;
   c) operating the computer together with the second program to calculate certain properties of the petroleum fraction or hydrocarbon mixture feedstock selected for the petroleum fraction or hydrocarbon mixture from the analytical data of step a) that match the average analytical properties of the hydrocarbon mixture;
   d) running the process simulation program using the calculated properties of the petroleum fraction or hydrocarbon mixture of step b) with various selected operating parameters until a desired process result or performance is obtained;
   e) selecting those operating parameters of step d) that were used to obtain the desired result or performance and entering them into the operating system of the refinery process for separation or conversion of components of a petroleum fraction or hydrocarbon mixture; and
wherein the computer subprogram comprises those that are capable of calculating a calculated hydrocarbon mixture obtained from predetermined analytical data comprising:
   a) providing a compilation of identified chemical pure or compound species for which a Shannon entropy may be calculated marked with identifiers and including chemical and physical properties, wherein compound species comprise a compilation of related molecules in chemical equilibrium, wherein the compound species chemical and physical properties are computed by group contribution methods, and wherein the composition of each pure or compound species in the hydrocarbon mixture that maximizes a Shannon entropy of the compilation is calculated by determining the composition ($X_i$) of each compound or compound species that maximizes the Shannon entropy of the mixture, S, by a model that satisfies the equation $$\max_X \left\{ S = -\sum_i X_i \cdot \mathrm{Ln}(X_i) \right\}$$

and satisfies the constraints imposed by the application of mixing rules by the equation $$\overline{P}_j = \sum_j X_i \cdot P_{i,j}$$

and calculating of the properties of the mixture to match the average properties of a sample hydrocarbon mixture, $P_j$;
   b) providing average analytical properties of a hydrocarbon mixture;
   c) selecting pure and compound species for a specific hydrocarbon mixture of interest;
   d) determining a composition of each pure or compound species in the hydrocarbon mixture having a Shannon entropy that maximizes the Shannon entropy of the hydrocarbon mixture and satisfies constraints imposed by the application of mixing rules;
   e) calculating properties of the hydrocarbon mixture that match the average analytical properties of the hydrocarbon mixture to produce calculated results; and
   f) arranging the calculated results of step e) in a tangible, non-transitory database and utilizing the database in the operation of the computerized program to calculate operating parameters and results of hydrocarbon processing units to enable the application of detailed kinetics and fundamental reactor models.

2. The method of claim 1 wherein the second non-transitory machine-readable program comprising a method capable of calculating a calculated hydrocarbon mixture obtained from predetermined analytical data include calculation of the compound species of step a) by a combination of group contribution and molecular connectivity methods.

3. The method of claim 1 wherein the second non-transitory machine-readable program comprising a method capable of calculating a calculated hydrocarbon mixture obtained from predetermined analytical data include calculation of the compound species of step a) wherein by a combination the hydrocarbon mixture comprises hydrocarbons having carbon numbers of 1 to 40.

4. The method of claim 1 wherein the refinery processes comprise one or more of distillation units, steam cracking units, pyrolysis, steam reforming units, catalytic cracking units, hydrocracking unit, catalytic reforming units, isomeration units and desulfuration units.

* * * * *